(12) United States Patent
Luaire et al.

(10) Patent No.: US 11,141,395 B2
(45) Date of Patent: Oct. 12, 2021

(54) HD ACID CONCENTRATE WITH AMINO ACIDS

(71) Applicant: FRESENIUS MEDICAL CARE DEUTSCHLAND GMBH, Bad Homburg (DE)

(72) Inventors: Benoit Luaire, Sourcieux les Mines (FR); Philippe Laffay, Sainte Foy les Lyon (FR); Charles Chazot, Saint-Genis-les-Ollieres (FR); Patrik Deleaval, Messimy (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/317,832

(22) PCT Filed: Jul. 21, 2017

(86) PCT No.: PCT/EP2017/068467
§ 371 (c)(1),
(2) Date: Jan. 15, 2019

(87) PCT Pub. No.: WO2018/015531
PCT Pub. Date: Jan. 25, 2018

(65) Prior Publication Data
US 2020/0352888 A1 Nov. 12, 2020

(30) Foreign Application Priority Data

Jul. 22, 2016 (EP) ..................................... 16001614
Jul. 22, 2016 (EP) ..................................... 16290142

(51) Int. Cl.
*A61K 31/198* (2006.01)
*A61M 1/16* (2006.01)
(Continued)

(52) U.S. Cl.
CPC .......... *A61K 31/198* (2013.01); *A61K 31/405* (2013.01); *A61K 31/4172* (2013.01);
(Continued)

(58) Field of Classification Search
CPC .... A61K 31/405; A61K 45/06; A61K 31/198; A61K 31/7004; A61K 33/06;
(Continued)

(56) References Cited

FOREIGN PATENT DOCUMENTS

| CA | 2259623 A1 | 10/1998 |
|---|---|---|
| CN | 1813718 A | 8/2006 |

(Continued)

OTHER PUBLICATIONS

Machine Translation, Eng. CN1813718 A, Yu Lili, Aug. 2006.*
Yu Lili (CN 1813718 A, using Eng. Translation (Machine)), 2006 (Year: 2006).*
(Continued)

*Primary Examiner* — Blessing M Fubara
(74) *Attorney, Agent, or Firm* — Kilyk & Bowersox, P.L.L.C.

(57) ABSTRACT

A precursor composition for the preparation of a dialysis fluid, the precursor composition comprising at least a glucose component, an acid component, and an amino acid component, wherein the amino acid component comprises Valine, Isoleucine and Leucine.

16 Claims, 1 Drawing Sheet

(51) Int. Cl.
    *A61K 31/405*     (2006.01)
    *A61K 31/4172*     (2006.01)
    *A61K 31/7004*     (2006.01)
    *A61K 33/00*     (2006.01)
    *A61K 33/06*     (2006.01)
    *A61K 33/14*     (2006.01)

(52) U.S. Cl.
    CPC .......... *A61K 31/7004* (2013.01); *A61K 33/00* (2013.01); *A61K 33/06* (2013.01); *A61K 33/14* (2013.01); *A61M 1/1666* (2014.02)

(58) Field of Classification Search
    CPC .... A61K 33/00; A61K 31/4172; A61K 33/14; A61K 2300/00; A61M 1/1666; A61P 7/08; A61P 3/02
    See application file for complete search history.

(56) References Cited

FOREIGN PATENT DOCUMENTS

| | | |
|---|---|---|
| EP | 1714657 A1 | 10/2006 |
| EP | 2905039 A1 | 8/2015 |
| JP | 2005330241 A | 12/2005 |

OTHER PUBLICATIONS

Tjiong et al. "Peritoneal Dialysis with Solutions Containing Amino Acids Plus Glucose Promotes Protein Synthesis during Oral Feeding" in Clinical Journal of American Society of Nephrology, 2: 74-80, 2007 (Year: 2007).*
International Search Report and Written Opinion issued in corresponding International Patent Application No. PCT/EP2017/068467 dated Dec. 22, 2017 (17 pages).

* cited by examiner

HD ACID CONCENTRATE WITH AMINO ACIDS

This application is a National Stage Application of PCT/EP2017/068467, filed Jul. 21, 2017, which claims priority to European Patent Application No. 16290142.5, filed Jul. 22, 2016 and European Patent Application No. 16001614.3, filed Jul. 22, 2016.

I. FIELD OF THE INVENTION

The invention relates to a precursor composition for the preparation of a dialysis fluid comprising an amino acid component. The invention further relates to a precursor composition comprising said amino acid component which, upon mixing with a buffer composition and aqueous dilution, yields a dialysis fluid. Said dialysis fluid may be used for the treatment of e.g. end stage renal therapy patients in hemodialysis. The invention further relates to the treatment of malnourished dialysis patients with said dialysis fluid.

II. BACKGROUND OF THE INVENTION

In dialysis treatments, dialysis fluids are used as an exchange medium to take up metabolite substances via a separation membrane from patient's blood plasma. Within dialysis treatments the blood plasma concentrations of electrolytes and glucose is controlled by substance exchange processes occurring between patient's blood and a respective dialysis fluid.

Dialysis fluids are aqueous fluids which contain solutes in a similar concentration to human blood plasma.

Commonly, a dialysis fluid comprises electrolytes like sodium chloride, optionally potassium chloride, magnesium chloride, calcium chloride, glucose and a buffer like sodium lactate or sodium bicarbonate. Dialysis fluids are offered in certain variations which are different in the concentration of dissolved ingredients. It can be important to treat dialysis patients with respective dialysis fluids due to arising comorbidities of dialysis patients, like blood hypertension, hyper and hypocalcaemia and others.

Dialysis fluids may be provided in ready-to-use product forms. For example, dialysis fluids may be provided in fluid bags. In hemodialysis therapy, dialysis fluids may also be provided by an online dialysis fluid preparation present in a respective dialysis treatment unit. Dialysis fluids are then prepared from precursor compositions by automated mixing and dilution processes.

Appropriate precursor compositions are known in the art. They are offered in packaged form, which makes it possible to directly connect these precursor composition packages to a respective dialysis treatment machine. These dialysis machines process said precursor compositions by diluting and proportional mixing respective volume fractions form the precursor composition to yield a ready-to-use dialysis fluid.

The commercial provision of precursor compositions suffer from certain drawbacks, as certain components of said precursor compositions cannot be stored together without causing harmful degradation processes. In this respect, the storage of glucose with a basic buffer like bicarbonate has shown to result in glucose degradation. Nevertheless, glucose and bicarbonate are the choice of components for hemodialysis, as both substances are well accepted from dialysis patients.

Glucose degradation products like 5-HMF are harmful and their presence in dialysis products is inacceptable. Thus, in development and production of precursor compositions, great care has to be taken that certain product configurations do not lead to degradation processes. Therefore, dialysis fluid products and respective precursor compositions are often offered in a two- or multi-compartment form to provide incompatible components, like glucose and bicarbonate, separately in different compartments.

It is known in the art to store the components of a precursor composition in compartments which comprise, in a first compartment, components like glucose, sodium, potassium, magnesium, calcium, hydrochloric acid, citric acid or acetic acid.

In a second compartment contributing to the precursor composition of the first compartment, a buffer is provided. The separation of respective components as explained here made it possible to offer stable shelf life dialysis precursor compositions.

In recent years, it has been an object to steadily improve the performance of hemodialysis therapies. As a result, extracorporal blood treatment has become more efficient and treatment times have been reduced. Efficient therapies in extracorporal blood treatment of dialysis patients nowadays comprise certain blood filtration processes, which efficiently remove harmful metabolites form patient's blood. It has been found that undesired blood plasma proteins ranging in the middle molecular weight range are efficiently removed from patient's blood by aforementioned blood treatment therapies, and state of health in dialysis patients could be improved.

On the other hand, some drawbacks from efficient hemodialysis therapies were identified. A known problem of chronical hemodialysis patients is malnutrition. Rocco et al. (Rocco et al.; Kidney International, Vol 65 (2004), pp. 2321-2334) observed a decline of body weight, albumin concentration in blood plasma and the uptake of proteins of dialysis patients over a time range of three years. It has been found that in particular the albumin level in blood is significant for the morbidity of patients.

Several pathologic indications are said to increase the protein metabolism of patients with kidney insufficiency (Dukkipati et al.; Seminars in Nephrology; Vol. 29, No. 1, January 2009, pp. 39-49) that may lead to protein catabolism of respective patients.

In addition, hemodialysis treatment is known to clear amino acids, the building blocks of proteins, from blood plasma. Amino acids are small molecules free of binding in blood plasma. They are removed from the plasma during the dialysis treatment session with a significant decline of their plasma concentration between the beginning and the end of a dialysis treatment session. If food intake of a dialysis patient is not sufficient, amino acid losses are not compensated enough and protein catabolism of said dialysis patient worsens. As a consequence, several actions were developed to compensate amino acid loss of dialysis patients.

In a first therapeutic measure, dialysis patients are served protein enriched food. In another measure, dialysis patients can be supplemented with an amino acid composition, for example by infusion. Infusion might be performed during a dialysis treatment session or independently of the treatments sessions. In a third measure, it was suggested to enrich dialysis fluids with amino acids.

However, nutrition of patients with protein enriched food affords a higher individual patient care. Another drawback is that a significant number of patients are not willing to take up protein enriched food during a dialysis treatment session. Also the protein enriched food is not well accepted by at least part of the patients.

The infusion of solutions of amino acid compositions to patients burdens the patient with an additional liquid volume which in consequence means that a higher ultrafiltration volume has to be removed from the patient during a dialysis treatment session. Thus, treatment times of patients have to be disadvantageously extended. Additionally, administration of infusion solutions increases the costs for treatment and efforts to the clinical staff.

Dialysis fluids comprising amino acid components known so far provide poor storage stability. It has been suggested to supply dialysis patients with amino acids by adding amino acids to the dialysis fluids shortly before a dialysis treatment session (U.S. Pat. No. 6,787,039). However, the addition of amino acids to a dialysis fluid always bears the risk of bio-contamination and incorrect dosing.

It was further observed that storage of amino acid components together with other components of a dialysis fluid or a precursor composition can induce decomposition reactions. The well-known Maillard decomposition reaction is initiated between glucose and amino acid components. This led to the conclusion that amino acid components in dialysis fluids or dialysis precursor compositions have to be stored separately from a glucose component to avoid said Maillard reaction. However, it is not possible to store an amino acid component together with the buffer component in one compartment, separated from glucose, as basic storage of an amino acid component will not satisfy the requirement of shelf life of dialysis fluids or dialysis precursor compositions.

An alternative option wherein the amino acid component is stored solely in a third compartment is undesirable, as the receiving units of dialysis treatment machines in the art are not configured to connect a third compartment.

Therefore, there is a need in the state of the art to overcome aforementioned deficiencies.

It has therefore been an object of the invention to provide a precursor composition for the preparation of a dialysis fluid comprising an amino acid component which is stable and can be provided together with an acid component and a glucose component in one compartment.

It has been a further object of the invention to provide a dialysis fluid comprising an amino acid composition which is useful for the treatment of dialysis patients suffering from impaired muscle metabolism, mal-nutrition or amino acid loss.

It has been a further object of the invention to provide a process for the preparation of a dialysis fluid from a precursor composition comprising a therapeutic effective amino acid component.

It has been a still further object of the invention to provide a process and materials useful for the preparation of a precursor composition comprising a therapeutically effective amino acid composition for the use in the preparation of dialysis fluids.

III. BRIEF DESCRIPTION AND DEFINITION OF THE INVENTION

Within the understanding of the present application, the term "solute" refers to substances dissolved in an aqueous liquid. In this respect, salts like sodium chloride, magnesium chloride, calcium chloride, sodium bicarbonate, potassium chloride, which respectively dissolve by dissociation into solvated ions, are referred to as solutes. Further, compounds like organic acids or amines, which dissolve by dissociation or protonation into ionic forms, are referred to as solutes. Within this meaning, also solvated ions themselves are referred to as "solutes". The term "solute" as used herein refers further to dissolved non-ionic substances like glucose.

The term "buffer" as referred to in the present application relates to a compound which is able to compensate an acidic environment within a certain pH value range. Commonly used buffers in dialysis are a bicarbonate buffer, lactate buffer, acetate buffer, citrate buffers, which are physiologically acceptable.

The term "acid" refers to a substance which is able to lower the pH value of water below pH 7 when dissolved. In particular, the term is used to specify an acid which can be metabolized by dialysis patients and is physiologically acceptable. Common physiologically acceptable acids in dialysis are citric acid, hydrochloric acid, and acetic acid. It is within the understanding of the present application to address acids in their dry and/or solid form, in dissolved form, in liquid form and any (other) form, as long as these forms provide a starting material for the preparation of a dialysis fluid.

The term "concentrate" refers to a composition which has to be mixed with an aqueous diluent prior to administering the resulting mixed solution to a patient. Concentrates may appear in dry form, which means that those concentrates comprise solid constituents. Within the meaning of the present invention, a dry concentrate may also comprise fluid constituents which are, for example, absorbed by solid granules or particles of the concentrate. Within the meaning of the invention, concentrates may also appear as liquid preparations. Concentrates are transferred into dialysis fluids by dilution with water or diluted aqueous solutions.

The term "component" refers to a constituent, which is present in a dialysis concentrate or a dialysis fluid. A component may comprise a solute, e.g. sodium chloride, potassium chloride, magnesium chloride, calcium chloride. A component may also be composed of more than one constituent, e.g. an amino acid component as a part of a dialysis concentrate or a dialysis fluid.

The term "precursor composition" as used herein refers to a composition of constituents which serve as a starting material in a process for the preparation of a fluid which may be used as a treatment fluid in dialysis therapies. A precursor composition may comprise several components or all components of solutes which are necessary for the preparation of a respective dialysis fluid. A precursor composition may be in form of a dry concentrate, a liquid concentrate or a solution which comprises respective components in concentrations already applicable in dialysis treatment sessions.

The term "dialysis fluid" relates to an aqueous formulation which is acceptable for dialysis patients for therapeutic use of blood purification. The composition and requirements of dialysis fluids are regulated in the monography of the European Pharmacopoeia. Within the understanding of the present application, a dialysis fluid may be obtained from a precursor composition by steps of diluting or mixing with further components in a form ready-to-use in dialysis treatment sessions.

Surprisingly, it has been found that, in a first aspect of the invention, the problem according to an aforementioned object of the invention is solved by a precursor composition comprising at least a glucose component, an acid component, and an amino acid component, wherein the amino acid component comprises Valine, Isoleucine and Leucine.

In a further embodiment of the first aspect of the invention the precursor composition is characterized in that if the amino acid component comprises Methionine or Tryptophan or Methionine and Tryptophan the precursor composition is packaged and stored so that the precursor composition is kept at ambient temperature and shielded from UV light and oxygen.

In a further embodiment of the first aspect of the invention, the precursor composition is characterized in that the precursor composition further comprises sodium chloride.

In a further embodiment of the first aspect of the invention, the precursor composition is characterized in that the precursor composition is in the form of a dry, e.g. in granular or powder form, or a liquid concentrate.

In a further embodiment of the first aspect of the invention, the precursor composition is characterized in that the precursor composition further comprises at least one cation selected from potassium, calcium and magnesium, e.g. potassium, calcium and magnesium, and an acid component selected from citric acid, acetic acid, hydrochloric acid and succinic acid.

In a further embodiment of the first aspect of the invention, the precursor composition is characterized in that the amino acid component comprises Leucine, Isoleucine, Valine and at least one of the Phenylalanine, Methionine, Lysine, Threonine, Tryptophan and Histidine, or comprises all of the afore-mentioned amino acids, or consists of Leucine, Isoleucine, Valine, Phenylalanine, Methionine, Lysine, Threonine, Tryptophan and Histidine and is present in an amount to yield upon mixing with a diluent in a dialysis fluid.

| Amino Acid | Concentration range |
| --- | --- |
| Leucine | 110 to 160 µmole/l |
| Isoleucine | 54 to 75 µmole/l |
| Valine | 210 to 290 µmole/l |
| Phenylalanine | 35 to 75 µmole/l |
| Methionine | 10 to 30 µmole/l |
| Lysine | 110 to 200 µmole/l |
| Threonine | 80 to 150 µmole/l |
| Tryptophan | 20 to 150 µmole/l |
| Histidine | 50 to 100 µmole/l |

In a further embodiment of the first aspect of the invention, the precursor composition is characterized in that the amino acid component is free from Methionine or Tryptophan or that the amino acid component is free from Methionine and Tryptophan. In one embodiment the amino acid component is present in the precursor composition which is free of tryptophan to yield upon mixing with a diluent in a dialysis fluid exhibiting the following amino acid concentration ranges:

| Amino Acid | Concentration range |
| --- | --- |
| Leucine | 110 to 160 µmole/l |
| Isoleucine | 54 to 75 µmole/l |
| Valine | 210 to 290 µmole/l |
| Phenylalanine | 35 to 75 µmole/l |
| Methionine | 10 to 30 µmole/l |
| Lysine | 110 to 200 µmole/l |
| Threonine | 80 to 150 µmole/l |
| Histidine | 50 to 100 µmole/l |

In one further embodiment of the first aspect of the invention the precursor composition is characterized in that the amino acid component consists of the eight amino acids Leucine, Isoleucine, Valine, Phenylalanine, Methionine, Lysine, Threonine, Histidine.

In one further embodiment of the first aspect of the invention the precursor composition is characterized in that the amino acid component comprises or consists of the seven amino acids Leucine, Isoleucine, Valine, Phenylalanine, Lysine, Threonine, Histidine.

In one embodiment of the first aspect of the invention the amino acid component is present in the precursor composition which is free of tryptophan and methionine to yield upon mixing with a diluent in a dialysis fluid exhibiting the following amino acid concentration ranges:

| Amino Acid | Concentration range |
| --- | --- |
| Leucine | 110 to 160 µmole/l |
| Isoleucine | 54 to 75 µmole/l |
| Valine | 210 to 290 µmole/l |
| Phenylalanine | 35 to 75 µmole/l |
| Lysine | 110 to 200 µmole/l |
| Threonine | 80 to 150 µmole/l |
| Histidine | 50 to 100 µmole/l |

In a further embodiment of the first aspect of the invention, the precursor composition is characterized in that the amino acid component consists of Valine, Leucine and Isoleucine.

In a further embodiment of the first aspect of the invention, the precursor composition is characterized in that the amino acid component consists of Valine, Leucine and Isoleucine and is present in an amount to yield upon mixing with a diluent in a dialysis fluid the respective amino acid concentration ranges of

| Amio Acid | Concentration |
| --- | --- |
| Leucine | 110 to 160 µmole/l |
| Isoleucine | 54 to 75 µmole/l |
| Valine | 210 to 290 µmole/l |

In a further embodiment of the first aspect of the invention, the precursor composition is characterized in that the amino acid component consists of Valine, Leucine and Isoleucine and is present in an amount to yield upon mixing with a diluent in a dialysis fluid the respective amino acid concentration ranges of

| Amio Acid | Concentration |
| --- | --- |
| Leucine | 120 to 140 µmole/l |
| Isoleucine | 65 to 75 µmole/l |
| Valine | 260 to 280 µmole/l. |

In a further embodiment of the first aspect of the invention, the precursor composition is characterized in that the amino acid component consists of Valine, Leucine and Isoleucine and is present in an amount to yield upon mixing with a diluent in a dialysis fluid the respective amino acid concentration ranges of

| Amio Acid | Concentration |
| --- | --- |
| Leucine | 300 to 370 µmole/l |
| Isoleucine | 180 to 240 µmole/l |
| Valine | 580 to 680 µmole/l |

In a further embodiment of the first aspect of the invention, the precursor composition is present in packaged form and, after being exposed to a temperature of 40° C. and a relative air humidity of 25% for 9 months, yields a 5-HMF concentration of below 18 mg/l when prepared to yield a dialysis fluid.

In a further embodiment of the first aspect of the invention, the precursor composition is characterized in that respective components of the precursor composition are present in an amount to yield a dialysis fluid exhibiting the following concentration ranges

| Component | Concentration |
| --- | --- |
| Citric Acid | 1 to 20 mmole/l |
| Glucose | 0.8 to 2.2 g/l |
| Sodium | 110 to 170 mmole/l |
| Potassium | 0.7 to 4.3 mmole/l |
| Magnesium | 0.3 to 1.2 mmole/l |
| Calcium | 0.1 to 2.2 mmole/l |
| Valine | 110 to 160 µmole/l |
| Leucine | 54 to 80 µmole/l |
| Isoleucine | 210 to 290 µmole/l. |

In a further embodiment of the first aspect of the invention, the precursor composition is characterized in that the respective components of the precursor composition are present in an amount to yield a dialysis fluid exhibiting the following concentration ranges

| Component | Concentration |
| --- | --- |
| Citric Acid | 1 to 15 mmole/l |
| Glucose | 1 to 2 g/l |
| Sodium | 125 to 145 mmole/l |
| Potassium | 2 to 3 mmole/l |
| Magnesium | 0.5 to 1 mmole/l |
| Calcium | 1.25 to 1.75 mmole/l |
| Valine | 120 to 140 µmole/l |
| Leucine | 65 to 75 µmole/l |
| Isoleucine | 260 to 280 µmole/l. |

In a second aspect of the invention, it has been found that the problem according to an aforementioned object of the invention is solved by a process of manufacturing a dialysis fluid comprising the steps:
i. providing a precursor composition to any aforementioned embodiments of the first aspect of the invention,
ii. providing a buffer composition,
iii. optionally, providing a diluent,
iv. mixing said precursor composition, said buffer composition and optionally said diluent by proportional mixing of liquid volume fractions of said composition of step i. and ii. and optionally iii. to yield a dialysis fluid.

In a third aspect of the invention, it has been found that the problem according to an aforementioned object of the invention is solved by a pre-granulate for preparing a precursor composition according to any of the embodiments of the first aspect of the invention, wherein the pre-granulate comprises an amino acid component comprising Valine, Leucine and Isoleucine and a sodium chloride component, wherein the sodium chloride content in said pre-granluate ranges from 10% to 80% or preferable from 60% to 50% per weight.

In a fourth aspect of the invention, it has been found that the problem according to an aforementioned object of the invention is solved by a process for producing a precursor composition according to any of the aforementioned embodiments of the first aspect of the invention, comprising the steps:

i. providing an amino acid component comprising at least Valine, Leucine and Isoleucine,
ii. providing a sodium chloride component in dry salt form,
iii. compounding said amino acid component and said sodium chloride component to obtain a compound,
iv. performing granulation of said compound to form a pre-granulate, comprising a mixture of said amino acid component and said sodium chloride component,
v. providing further components of glucose and an acid,
vi. mixing or compounding and performing a further granulation of components of step v. and said pre-granulate obtained in step iv. to obtain a precursor composition in dry form
or
dissolving said components of step v. and said pre-granulate obtained in step iv. in water to obtain said precursor composition in liquid form.

In a further embodiment of the fourth aspect of the invention, the process for producing a precursor composition is characterized in that the sodium chloride concentration in said pre-granulate is adjusted to yield a ratio from 10% to 80%, preferably 20% to 60% by weight of the total weight of the obtained pre-granulate.

In a fifth aspect of the invention, it has been found that the problem according to an aforementioned object of the invention is solved by a dialysis fluid comprising the amino acids Valine, Leucine, Isoleucine in an amount of

| Amio Acid | Concentration Range |
| --- | --- |
| Leucine | 300 to 370 µmole/l |
| Isoleucine | 180 to 240 µmole/l |
| Valine | 580 to 680 µmole/l | for use in the treatment of dialysis patients suffering from impaired muscle metabolism.

IV. DETAILED DESCRIPTION OF THE INVENTION

Surprisingly, in a first aspect of the invention, the above mentioned object could be met by a precursor composition comprising an amino acid component which, upon mixing with a buffer component and dilution, yields a dialysis fluid. The precursor composition comprises at least a glucose component, an acid component and an amino acid component comprising Valine, Leucine and Isoleucine. The inventors have found that the combination of Valine, Leucine and Isoleucine in presence of glucose and an acid does not lead to adverse amino acid decomposition or glucose degradation. Therefore, it has been possible to provide a precursor composition which comprises said glucose acid and amino acid components in one compartment without inacceptable detrimental reactions during shelf life.

In one embodiment of the invention according to the first aspect of the invention, said precursor composition is provided as a concentrate composition. Dialysis concentrate compositions can be distributed as lightweight products. Respective dialysis facilities and dialysis treatment machines are equipped to provide purified reverse osmosis water or simple tab water sources to supply the respective dialysis treatment machines with the needed volume of water for the preparation of dialysis fluids.

In a further embodiment of the invention according to the first aspect, the precursor composition is provided in powder or granular form as a dry concentrate or is provided as a liquid concentrate comprising said amino acid component, an acid component, a glucose component and a sodium chloride component. The inventors have found that the amino acid component can be added to the other precursor composition components during the process of producing the precursor composition. Preferably, the amino acid component can be compounded in a granulation process together with the other precursor composition components without detrimental decomposition reactions. It was found that the resulting precursor composition in dry granular form can be dissolved efficiently in short times in water when compounded with sodium chloride. As a result, the granulation together with sodium chloride salt provides granulates wherein the precursor composition components are mixed and distributed within each respective granule. Dissolution of said granulates is efficiently performed in short times because of the fast dissolving sodium chloride.

In a further aspect of the invention according to the first aspect, the precursor composition in liquid concentrate form comprises also sodium chloride in dissolved form. Sodium is a relevant component in dialysis fluids. Dialysis treatment with dialysis fluids containing sodium chloride show an impact on the sodium balance of a dialysis patient blood plasma and may therefore serve to control blood pressure of treated dialysis patients.

In a further embodiment of the first aspect of the invention the precursor composition includes further substances which are relevant for dialysis. The further components may be potassium, magnesium and calcium, for example in their respective chloride salt forms or in dissolved electrolyte form, in a respective dry or liquid form of the precursor composition. Potassium, calcium and magnesium are important to maintain the physiologic electrolyte balance of dialysis patients. Further, dialysis patients suffering from certain comorbidities like hyperkalaemia or hypocalcaemia and others can be treated by an adapted composition of the respective components in the precursor composition.

In one further embodiment of the first aspect, the acid component is chosen from the group consisting of citric acid, acetic acid, hydrochloride acid and succinic acid. Hydrochloride acid is commonly used for liquid precursor composition, as hydrochloride acid is obtainable in liquid form and is physiologically well accepted by dialysis patients. Citric acid is also a well-accepted acid component. Citric acid is a solid acid. As such it can be easily implemented in granulation processes which may be part of the production of the precursor composition. In addition, citric acid has a beneficial effect on dialysis patients' blood coagulation tendency when coming into contact with the patient's blood during a dialysis treatment session.

Another useful acid component which has shown to be compatible to amino acid components according to the present invention is acetic acid. Acetic acid is liquid at ambient temperatures and may be suitable for both the preparation of solid and liquid precursor compositions comprising said amino acid composition. In dry precursor compositions, the amount of acetic acid is kept as low as to be adsorbed by other solid components, like sodium chloride, present in said composition. The overall appearance of such granules or powders remains still solid but is characterized by a certain moisture content resulting from acetic acid.

In a further embodiment of the first aspect of the invention, the stability of the precursor composition is further enhanced by removing any oxidation and temperature sensitive amino acids from said amino acid component. In this respect, it is in particular an object to provide an amino acid component which is free from Tryptophan or Methionine or which is free from Tryptophan and Methionine.

In a further embodiment of the first aspect of the invention, it was found that an even more stable precursor composition comprising an amino acid component, an acid component, glucose component and optionally further components as mentioned herein before could be obtained if the amino acid component consists of Valine, Leucine and Isoleucine in dry or liquid forms. With respect to the medical indication of impaired muscle metabolism, the precursor composition according to this embodiment is still effective to contribute to the treatment of dialysis patients suffering from amino acid loss, muscle metabolism diseases or malnutrition.

In a still further embodiment of the first aspect of the invention, said precursor composition according to any aforementioned embodiments is configured to yield a dialysis fluid upon mixing with a further buffer component and dilution with water to exhibit the following ranges of concentrations:

TABLE 1

| Amio Acid | Concentration Range |
| --- | --- |
| Leucine | 110 to 160 or 120 to 140 µmole/l |
| Isoleucine | 54 to 80 or 65 to 75 µmole/l |
| Valine | 210 to 290 or 260 to 280 µmole/l |

Concentrations of amino acids in ready-to-use dialysis fluids are adapted to the blood plasma concentration ranges. Dialysis fluids according to this embodiment are intended to prevent an amino acid loss during a dialysis treatment session.

In an alternative embodiment, a precursor composition is provided to yield a dialysis fluid which exhibits a concentration of amino acids in an about threefold amount of aforementioned concentrations:

TABLE 2

| Amio Acid | Concentration Range |
| --- | --- |
| Leucine | 300 to 370 µmole/l |
| Isoleucine | 180 to 240 µmole/l |
| Valine | 580 to 680 µmole/l |

It was found that an amino acid concentration of Leucine, Isoleucine and Valine in dialysis fluids that is about three times the amount of the concentration in blood plasma is effective to improve the physical constitution of patients, which suffer from impaired muscle metabolism.

In a further embodiment of the first aspect of the invention, the composition of the precursor composition according to any of the aforementioned embodiments is chosen to yield concentration ranges as indicated below when in admixture with a buffer and optionally a diluent:

TABLE 3

| Component | Concentration, common and preferred ranges |
| --- | --- |
| Acid | 1 to 20, 1 to 15 mole/l (e.g. citric acid) |
| Glucose | 0.8 to 2.2 g/l, 1 to 2 g/l |
| Sodium | 110 to 170 mmole/l, 125 to 145 mmole/l |
| Potassium | 0.7 to 4.3 mmole/l, 2 to 3 mmole/l |
| Magnesium | 0.3 to 1.2 mmole/l 0.5 to 1 mmole/l |
| Calcium | 0.1 to 2.2 mmole/l, 1.25 to 1.75 mmole/l |
| Valine | 110 to 160, 120 to 140 μmole/l |
| Leucine | 54 to 80, 65 to 75 μmole/l |
| Isoleucine | 210 to 290, 260 to 280 μmole/l |

In an alternative embodiment of the composition according to Table 3, Valine, Isoleucine and Leucine may be present in the threefold concentration according to Table 2 while maintaining the concentration of the other constituents in accordance with Table 3. It is also understood that the acid concentration relates to the concentration of [H$^+$] which may be present by dissociation, i.e. regarding a polyacid like citric acid, which is a tribasic acid, the concentration in Table 3 refers to the amount of dissociated [H$^+$] ions and not to the citrate concentration.

It was found that the above mentioned components can form together a precursor composition which is stable in respect of glucose or amino acid induced side reactions.

In a second aspect of the invention, it was an object to provide a process for producing a dialysis fluid containing an amino acid component suitable for the treatment of dialysis patients suffering from metabolism disorders and/or malnutrition. In an embodiment of the invention according to the second aspect of the invention, the object was met by providing in a first process step a precursor composition comprising an amino acid component according to any of the aforementioned embodiments of the first aspect of the invention. In one embodiment, the precursor composition is housed in a container and is brought into fluid connection with a dialysis treatment machine. In a second step, a second container comprising a buffer composition is brought in fluid connection to said dialysis treatment unit. Optionally, the precursor composition and the buffer composition are diluted with controlled proportions of a diluent, which is ultra-purified water to yield a dialysis fluid with desired concentrations of electrolytes, glucose, buffer and amino acids at a desired pH value. Subsequently, the obtained dialysis fluid is ready for use, A preferred embodiment of the second aspect the invention is characterized in that the dialysis fluid comprises components in concentrations as listed below:

TABLE 4

| Component | Concentration, common and preferred ranges |
| --- | --- |
| Acid | 1 to 20, 1 to 15 mole/l (e.g. citric acid) |
| Glucose | 0.8 to 2.2 g/l, 1 to 2 g/l |
| Sodium | 110 to 170 mmole/l, 125 to 145 mmole/l |
| Potassium | 0.7 to 4.3 mmole/l, 2 to 3 mmole/l |
| Magnesium | 0.3 to 1.2 mmole/l 0.5 to 1 mmole/l |
| Calcium | 0.1 to 2.2 mmole/l, 1.25 to 1.75 mmole/l |
| Valine | 110 to 160, 120 to 140 μmole/l |
| Leucine | 54 to 80, 65 to 75 μmole/l |
| Isoleucine | 210 to 290, 260 to 280 μmole/l |

A precursor composition according to the first aspect of the invention may be manufactured by adding the amino acid component dissolved in water, comprising at least the amino acids Valine, Leucine and Isoleucine. The dissolved amino acid composition can be added during the production of a liquid precursor composition corresponding for example to dialysis fluids of Table 5 and Table 6.

Alternatively, the amino acid component may be injected during the filling process of liquid precursor composition into fluid bag packaging to form a precursor composition according to the invention.

However, dissolved amino acids are susceptible to biocontamination and may require additional disinfection steps in order to provide them in a necessary purified form. Additionally, storage of dissolved amino acids without stabilisation may be problematic due to their degradation tendencies in the dissolved state. Although amino acids are characterized by sufficient storage stability in the dry state, the use of dry amino acids in the production of a dialysis precursor composition is cumbersome due to the laborious process of dosing amino acids in powdery form. Such dosing techniques suffer from the risk of producing dosing failures.

In a third aspect of the invention, an above mentioned object could be met by a pre-granulate for preparing a precursor composition according to any embodiment of the first aspect of the invention. The pre-granulate is made from a compound which comprises a sodium chloride component in a ratio of 10% to 80% by weight of the total weight of the granulate and an amino acid component comprising Valine, Leucine and Isoleucine. In a preferred embodiment, the pre-granulate is characterized by a sodium chloride content of 20% to 60% per weight.

In a fourth aspect of the invention, it has been found that the above mentioned drawbacks could be overcome in a new process for producing a precursor composition according to the first aspect of the invention. The production process is characterized by a first step of compounding a dry amino acid component together with a sodium chloride salt component. Compounding within the present invention means to mix at least two components, i.e. the amino acid component and the sodium chloride salt component, in a dry or in liquid solution state to form an admixture. The admixture is dried, when in liquid or moist form, by known techniques to form a solid conglomerate of said components, i.e. the amino acid component and said sodium chloride salt. Subsequently, the obtained conglomerate is formed to a pre-granulate in a granulation process.

It is preferred that the ratio of sodium chloride in said pre-granulate is about 30% by weight related to the total weight of the compounded pre-granulate. It is, however, also within the scope of the invention to choose a sodium chloride ratio for the pre-granulation in the range of 10% to 80% or 20% to 60% by weight. The compounded pre-granulate is advantageous in usage throughout the production of the precursor composition. Said pre-granulate allows more precise dosing in automated production processes, as granulates provide improved bulk pouring and handling properties. In addition, the pre-granulate provides the needed amounts of amino acid component distributed in a higher bulk volume compared to the provision of pure powdery amino acids as a starting material. Thus, weighing of desired amounts of said amino acids can be performed more precisely. Further, said pre-granulate is less sensitive to moisture impact during production processes and is characterized by short dissolution times when mixed with a liquid precursor composition of the invention.

Subsequently, the obtained dry pre-granulate can be used for the production of a liquid or dry precursor compositions according to any aforementioned embodiments of the first aspect of the invention.

In exemplary cases, compositions of dialysis fluids may contain citrate ions, originating from a citric acid precursor, bicarbonate ions, originating from a buffer composition comprising sodium bicarbonate, electrolytes and glucose, in concentrations as listed in Table 5:

TABLE 5

| Na$^+$ mmol/L | K$^+$ mmol/L | Ca$^{2+}$ mmol/L | Mg$^{2+}$ mmol/L | Cl$^-$ mmol/L | HCO$_3^-$ mmol/L | Citrate mmol/L | Acetate mmol/L | Glucose g/L |
|---|---|---|---|---|---|---|---|---|
| 138.00 | 2.00 | 1.50 | 0.50 | 109.00 | 32.00 | 1.00 | — | 1.00 |
| 138.00 | 2.00 | 1.75 | 0.50 | 109.50 | 32.00 | 1.00 | — | 1.00 |
| 138.00 | 3.00 | 1.50 | 0.50 | 110.00 | 32.00 | 1.00 | — | 1.00 |
| 138.00 | 3.00 | 1.75 | 0.50 | 110.50 | 32.00 | 1.00 | — | 1.00 |
| 138.00 | 4.00 | 1.50 | 0.50 | 111.00 | 32.00 | 1.00 | — | 1.00 |

Table 5 lists different concentration combinations of dissolved components. It is within the understanding of the present invention that the specifications in Table 5 do not outline all possible dialysis fluid solute concentrations. It may be necessary to envision further solute concentrations for therapeutic reasons.

Other exemplary dialysis fluids may contain acetate ions, originating from an acetic acid precursor, and bicarbonate ions, originating from a buffer composition comprising sodium chloride, as listed in Table 6:

TABLE 6

| Na$^+$ mmol/L | K$^+$ mmol/L | Ca$^{2+}$ mmol/L | Mg$^{2+}$ mmol/L | Cl$^-$ mmol/L | HCO$_3^-$ mmol/L | Acetate mmol/L | Glucose g/L |
|---|---|---|---|---|---|---|---|
| 138.00 | 1.00 | 1.50 | 0.5 | 108.00 | 32.00 | 3.00 | 1.00 |
| 138.00 | 2.00 | 1.25 | 0.5 | 108.50 | 32.00 | 3.00 | 1.00 |
| 138.00 | 2.00 | 1.50 | 0.5 | 109.00 | 32.00 | 3.00 | 1.00 |
| 138.00 | 2.00 | 1.75 | 0.5 | 109.50 | 32.00 | 3.00 | 1.00 |
| 138.00 | 3.00 | 1.25 | 0.5 | 109.50 | 32.00 | 3.00 | 1.00 |
| 138.00 | 3.00 | 1.50 | 0.5 | 110.00 | 32.00 | 3.00 | 1.00 |
| 138.00 | 4.00 | 1.25 | 0.5 | 110.50 | 32.00 | 3.00 | 1.00 |

The dialysis fluid concentrations as presented in Table 5 and Table 6 may be obtained from dry or liquid concentrate compositions. Said concentrate compositions are commonly offered in fluid bags or in rigid cartridges. Liquid concentrates are for example available in a 45-fold or a 35-fold concentration. That means that one volume part of the liquid concentrate is diluted with 44 respectively 34 volume parts of a diluting fluid like water.

It is understood herein that the diluting fluid may also be an aqueous solution of other dialysis fluid components. A common buffer provided in dialysis may be for example a bicarbonate solution which, upon proportioned mixing with respective precursor composition and optionally dilution, yields in ready-to-use dialysis fluid with desired composition as shown in Table 5 and Table 6.

V. EXAMPLES

Example 1

A precursor composition, resulting in dialysis fluids as listed in Table 5 or Table 6, was combined with an amino acid component containing Valine, Leucine and Isoleucine. The amino acid component was added in an amount to yield concentrations of

TABLE 5

| Amio Acid | Concentration |
|---|---|
| Leucine | 130 µmole/l |
| Isoleucine | 70 µmole/l |
| Valine | 270 µmole/ll | in a dialysis fluid corresponding to listed concentrations of Table 5 or Table 6.

Accordingly, a liquid precursor composition offered in a 45-fold concentration exhibited the following concentrations:

TABLE 6

| Component | Concentration |
|---|---|
| Sodium | 4.77 mole/l |
| Potassium | 45 mmole/l |
| Calcium | 67.5 mmole |
| Magnesium | 22.5 mmole/l |
| Chloride | 4.86 mole/l |
| Acetic acid | 135 mmole/l |
| Glucose | 45 g/l |
| Valine | 12.15 mmole/l |
| Leucine | 5.85 mmole/l |
| Isoleucine | 3.15 mmole/l |

The composition as listed above is configured to be diluted together with sodium bicarbonate and water as diluent to yield a dialysis solution with electrolyte, glucose, buffer and acetate concentrations as listed in row 1 of Table 6.

Example 2

Within this Example, the amino acid component comprises nine amino acids essential for the protein metabolism of humans, in particular essential for malnourished dialysis patients. According to this Example, the precursor composition may comprise Leucine, Isoleucine, Valine, Phenylalanine, Methionine, Lysine, Threonine, Tryptophan, Histidine in an amount to yield upon dilution and mixing with a buffer component a dialysis solution which exhibits concentrations of the respective amino acids as listed below:

TABLE 7

| Amino Acid | Concentration |
|---|---|
| Leucine | 130 µmole/l |
| Isoleucine | 70 µmole/l |
| Valine | 270 µmole/l |
| Phenylalanine | 60 µmole/l |
| Methionine | 30 µmole/l |
| Lysine | 180 µmole/l |
| Threonine | 150 µmole/l |
| Tryptophan | 50 µmole/l |
| Histidine | 80 µmole/l |

The storage of Methionine and Tryptophan among the remaining amino acids and in presence of an acid and glucose in the concentrate composition is crucial. However, the inventors have found that the appropriate ratios of amino acids present in the liquid or dry precursor composition prevented decomposition reactions of said amino acids. A shelf life product of a packaged concentrate composition according to the invention comprising above listed essential amino acids could be obtained in keeping the concentrate composition at ambient temperature, shielded from UV light and oxygen.

In a first trial a precursor composition comprising acetic acid as an acid component, which upon diluting and mixing with an bicarbonate component, results in a dialysis fluids as listed in Table 6, was combined with an amino acid component containing 9 amino acids Valine, Leucine and Isoleucine Phenylalanine, Methionine, Lysine, Threonine, Tryptophan and Histidine. Accordingly, a liquid precursor composition prepared in a 45-fold concentration exhibited the following concentrations:

| Component | Concentration |
|---|---|
| Sodium | 4.77 mole/l |
| Potassium | 45 mmole/l |
| Calcium | 67.5 mmole |
| Magnesium | 22.5 mmole/l |
| Chloride | 4.91 mole/l |
| Acetic acid | 135 mmole/l |
| Glucose | 45 g/l |
| Valine | 12.15 mmole/l |
| Leucine | 5.85 mmole/l |
| Isoleucine | 3.15 mmole/l |
| Phenylalanine | 2.7 mmole/l |
| Methionine | 1.35 mmole/l |
| Lysine | 8.1 mmole/l |
| Threonine | 6.75 mmole/l |
| Tryptophan | 2.225 mmole/l |
| Histidine | 3.6 mmole/l |

Figure 1:
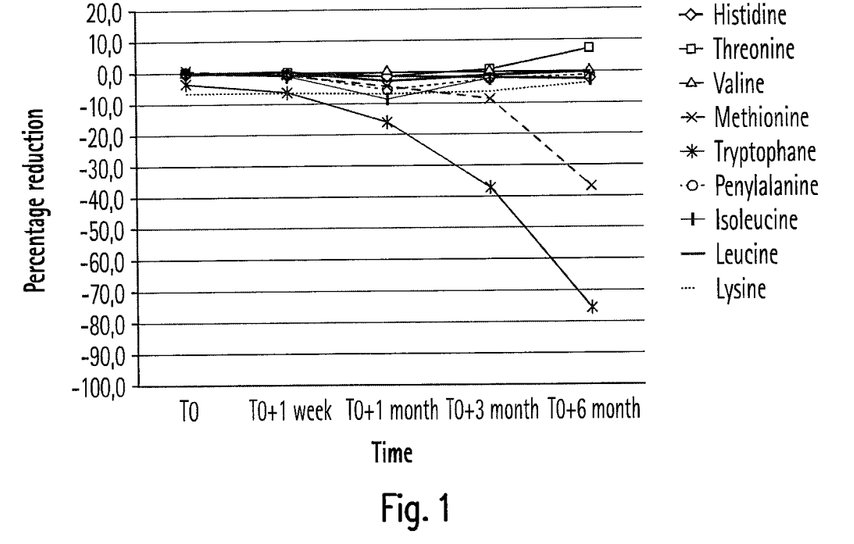
FIGS. 1 and 2 are graphs that each show the time dependent amino acid reduction in the precursor composition according to trials as set forth in the examples.

The amino acid component was added in an amount to yield concentrations of table Table 9 in the ready-to-use dialysis fluid. Stability tests were performed to approve the stability of the precursor composition. Precursor compositions were packaged and stored under ageing conditions. The packaged precursor compositions were stored under the climatic conditions described in example 4. The samples were exposed to said climate for 6 month. During the stability test, samples were inspected with regard to amino acid degradation. Amino acid stability was determined in percentage reduction of the respective amino acids. The percentage reduction in the precursor composition is depicted in FIG. 1. FIG. 1 shows the time dependent amino acid reduction in the precursor composition according to the second trial.

Figure 2:
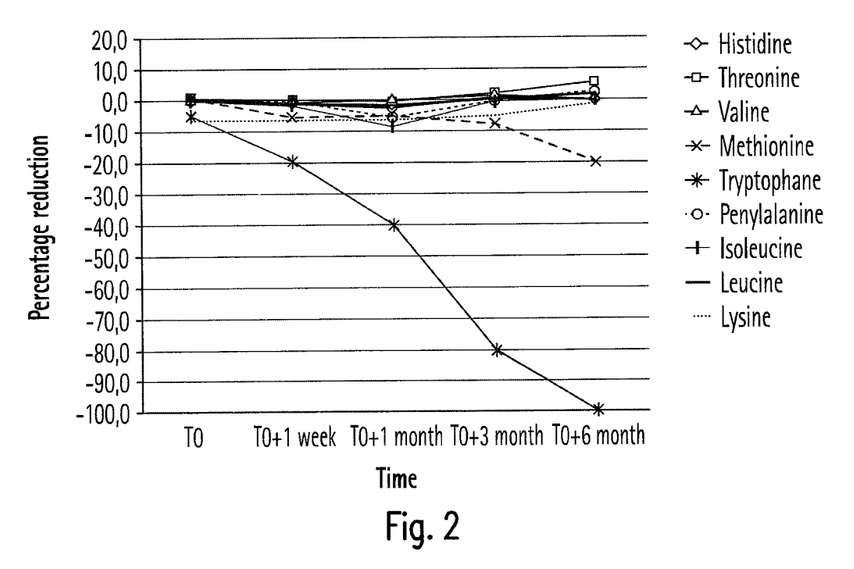

In a second trial a precursor composition, resulting in dialysis fluids as listed in Table 5, was combined with an amino acid component containing 9 amino acids Valine, Leucine and Isoleucine Phenylalanine, Methionine, Lysine, Threonine, Tryptophan and Histidine. Accordingly, a liquid precursor composition prepared in a 45-fold concentration exhibited the following concentrations:

| Component | Concentration |
|---|---|
| Sodium | 4.77 mole/l |
| Potassium | 45 mmole/l |
| Calcium | 67.5 mmole |
| Magnesium | 22.5 mmole/l |
| Chloride | 4.86 mole/l |
| Citric acid | 45 mmole/l |
| Glucose | 45 g/l |
| Valine | 12.15 mmole/l |
| Leucine | 5.85 mmole/l |
| Isoleucine | 3.15 mmole/l |
| Phenylalanine | 2.7 mmole/l |
| Methionine | 1.35 mmole/l |
| Lysine | 8.1 mmole/l |
| Threonine | 6.75 mmole/l |
| Tryptophan | 2.225 mmole/l |
| Histidine | 3.6 mmole/l |

The amino acid component was added in an amount to yield concentrations of Table 9. Stability tests were performed to approve the stability of the precursor composition. Precursor compositions were packaged and stored under ageing conditions. The packaged precursor compositions were stored under the climatic conditions described in example 4. The samples were exposed to said climate for 6 month. During the stability test, samples were inspected with regard to amino acid degradation. Amino acid stability was determined in percentage reduction of the respective amino acids. The percentage reduction in the precursor composition is depicted in FIG. 2. FIG. 2 shows the time dependent amino acid reduction in the precursor composition according to the second trial.

Example 3

A precursor composition, resulting in dialysis fluids as listed in Table 6, was combined with an amino acid component containing Valine, Leucine and Isoleucine Phenylalanine, Methionine, Lysine, Threonine, and Histidine. The amino acid component was added in an amount to yield concentrations of

| Amino Acid | Concentration |
|---|---|
| Leucine | 130 μmole/l |
| Isoleucine | 70 μmole/l |
| Valine | 270 μmole/l |
| Phenylalanine | 60 μmole/l |
| Methionine | 30 μmole/l |
| Lysine | 180 μmole/l |
| Threonine | 150 μmole/l |
| Histidine | 80 μmole/l | in a dialysis fluid corresponding to listed concentrations of Table 6. Accordingly, a liquid precursor composition with a 45-fold concentration exhibited the following concentrations:

| Component | Concentration |
|---|---|
| Sodium | 4.77 mole/l |
| Potassium | 45 mmole/l |
| Calcium | 67.5 mmole |
| Magnesium | 22.5 mmole/l |
| Chloride | 4.91 mole/l |
| Acetic acid | 135 mmole/l |
| Glucose | 45 g/l |
| Valine | 12.15 mmole/l |
| Leucine | 5.85 mmole/l |
| Isoleucine | 3.15 mmole/l |
| Phenylalanine | 2.7 mmole/l |
| Methionine | 1.35 mmole/l |
| Lysine | 8.1 mmole/l |
| Threonine | 6.75 mmole/l |
| Histidine | 3.6 mmole/l |

Example 4

Stability tests were performed to approve the stability of respective precursor compositions. Samples of precursor compositions comprising an amino acid component including Valine, Leucine and Isoleucine were packaged and stored under ageing conditions. The packaged precursor compositions were stored under adjusted climatic conditions of 40° C. and 25% relative air humidity at ambient atmospheric pressure. The samples were exposed to said climate for 9 months. During the stability test, samples were inspected with regard to indications of following instabilities:

- samples were checked in regard to visual indications of colorization, agglomeration and precipitation of components of the precursor composition
- concentrations and ratios of respective components of the precursor composition were monitored and it was recorded whether values shifted outside a specified tolerance range
- concentration tolerances were defined to the following ranges
  a. ±5% deviation from the initial ion concentration/ratio of electrolytes/salts (except for sodium ions)
  b. ±2.5% deviation from initial sodium ion/salt concentration/ratio
  c. ±10% deviation from the initial concentration/ratio of amino acids It was further monitored whether the concentration of 5-Hydroxymethylfurfural (5-HMF) remains below 18 mg/l, measured in a dialysis fluid sample prepared from an above described package. 5-HMF is an indicator of arising glucose decomposition.

The following results were obtained from stability studies of the aforementioned samples.

TABLE 8

Stability test results of a liquid concentrate composition comprising Valine, Leucine, Isoleucine, glucose and Acetic Acid (3 mmole/l in ready-to-use dialysis fluid)

| Component | Exposure = 0 | Exposure = 6 months | Exposure = 9 months |
| --- | --- | --- | --- |
| Amino acid | OK | OK | OK |
| Ion concentration | OK | OK | OK |
| Glucose degradation | OK | OK | OK |

TABLE 9

Stability test results of a liquid concentrate composition comprising Valine, Leucine, Isoleucine, Glucose and Citric acid (1 mmole/l in ready for use dialysis fluid)

| Component | Exposure = 0 | Exposure = 6 months | Exposure = 9 months |
| --- | --- | --- | --- |
| Amino acid | OK | OK | OK |
| Ion concentration | OK | OK | OK |
| Glucose degradation | OK | OK | acceptable |

TABLE 10

Stability test results of a liquid concentrate composition comprising Valine, Leucine/Isoleucine/(triple amino acid concentration) glucose and citric acid (1 mmole/l in ready-to-use dialysis fluid)

| Component | Exposure = 0 | Exposure = 6 months | Exposure = 9 months |
| --- | --- | --- | --- |
| Amino acid | OK | OK | OK |
| Ion concentration | OK | OK | OK |
| Glucose degradation | OK | acceptable | NOK |

Where a respective result of a stability investigation is assigned to "OK" in above Table 10 to Table 12, the required stability specification of a respective precursor composition is achieved. Where a result is found to be acceptable, the respective required stability specification can still be approved. Where a result is assigned to "NOK", the respective stability specification was not met.

Example 5

Stability tests were performed to approve the stability of a precursor composition comprising an amino acid component including eight amino acids Leucine, Isoleucine, Valine, Phenylalanine, Methionine, Lysine, Threonine, and Histidine. The precursor compositions were packaged and stored under ageing conditions. The packaged precursor compositions were stored under the same climatic conditions as described in example 4. The samples were exposed to said climate for 1 month. During the stability test, samples were inspected with regard to instabilities as explained in Example 4:

| Component | Exposure = 0 | Exposure = 1 months |
| --- | --- | --- |
| Amino acid | OK | OK |
| Ion concentration | OK | OK |
| Glucose degradation | OK | OK |

The invention claimed is:

1. A dialysis fluid precursor composition for the preparation of a dialysis fluid, the precursor composition comprising at least a glucose component, an acid component, and an amino acid component, wherein
the amino acid component comprises Valine, Isoleucine and Leucine, and the amino acid component is free from Methionine or Tryptophan or that the amino acid component is free from Methionine and Tryptophan.

2. The precursor composition according to claim 1, characterized in that the precursor composition further comprises sodium chloride.

3. The precursor composition according to claim 1, which is in the form of a dry form, or a liquid concentrate.

4. The precursor composition according to claim 2, characterized in that the precursor composition further comprises at least one cation selected from potassium, calcium and magnesium and an acid component selected from citric acid, acetic acid, hydrochloric acid and succinic acid.

5. The precursor composition according to claim 1, characterized in that the acid amino acid component comprises Leucine, Isoleucine, Valine, and at least one of Phenylalanine, Lysine, Threonine and Histidine, or comprises all of the aforementioned amino acids, or consists of Leucine, Isoleucine, Valine, Phenylalanine, Lysine, Threonine and Histidine.

6. The precursor composition according to claim 1, characterized in that the amino acid component consists of Valine, Leucine and Isoleucine, or the precursor composition is characterized in that the amino acid component consists of Valine, Leucine and Isoleucine, and is present in an amount to yield upon mixing with a diluent in a dialysis fluid the respective amino acid concentration ranges of

| Amio Acid | Concentration |
|---|---|
| Leucine | 110 to 160 µmole/l |
| Isoleucine | 54 to 75 µmole/l |
| Valine | 210 to 290 µmole/l, | or the precursor composition is characterized in that the amino acid component consists of Valine, Leucine and Isoleucine and is present in an amount to yield upon mixing with a diluent in a dialysis fluid the respective amino acid concentration ranges of

| Amio Acid | Concentration |
|---|---|
| Leucine | 120 to 140 µmole/l |
| Isoleucine | 65 to 75 µmole/l |
| Valine | 260 to 280 µmole/l, | or the precursor composition is characterized in that the amino acid component consists of Valine, Leucine and Isoleucine and is present in an amount to yield upon mixing with a diluent in a dialysis fluid the respective amino acid concentration ranges of

| Amio Acid | Concentration |
|---|---|
| Leucine | 300 to 370 µmole/l |
| Isoleucine | 180 to 240 µmole/l |
| Valine | 580 to 680 µmole/l. |

7. The precursor composition according to claim 1, characterized in that the precursor composition is present in packaged form, and after being exposed to a temperature of 40° C. and a relative air humidity of 25% for 9 months, yields a 5-Hydroxymethylfurfural concentration of below 18 mg/l when prepared to yield a dialysis fluid.

8. The precursor composition according to claim 1, characterized in that the respective components of the precursor composition are present in an amount to yield a dialysis fluid exhibiting the following concentration ranges

| Component | Concentration |
|---|---|
| Citric Acid | 1 to 20 mmole/l |
| Glucose | 0.8 to 2.2 g/l |
| Sodium | 110 to 170 mmole/l |
| Potassium | 0.7 to 4.3 mmole/l |
| Magnesium | 0.3 to 1.2 mmole/l |
| Calcium | 0.1 to 2.2 mmole/l |
| Valine | 110 to 160 µmole/l |
| Leucine | 54 to 80 µmole/l |
| Isoleucine | 210 to 290 µmole/l. |

9. The precursor composition according to claim 8, characterized in that the respective components of the precursor composition are present in an amount to yield a dialysis fluid exhibiting the following concentration ranges

| Component | Concentration |
|---|---|
| Citric Acid | 1 to 15 mmole/l |
| Glucose | 1 to 2 g/l |
| Sodium | 125 to 145 mmole/l |
| Potassium | 2 to 3 mmole/l |
| Magnesium | 0.5 to 1 mmole/l |
| Calcium | 1.25 to 1.75 mmole/l |
| Valine | 120 to 140 µmole/l |
| Leucine | 65 to 75 µmole/l |
| Isoleucine | 260 to 280 µmole/l. |

10. A process for manufacturing a dialysis fluid comprising the steps of
  i. providing the precursor composition according to claim 1,
  ii. providing a buffer composition,
  iii. optionally providing a diluent,
  iv. mixing said precursor composition, said buffer composition and optionally said diluent by proportional mixing of liquid volume fractions of the compositions of step i. and ii. and optionally iii. to yield a dialysis fluid.

11. A pre-granulate for preparing the precursor composition according to claim 1 being compounded of an amino acid component comprising Valine, Leucine and Isoleucine and a sodium chloride component characterized in that
  the sodium chloride content in said pre-granulate ranges from 10% to 80 by weight.

12. The pre-granulate of claim 11, where the sodium chloride content in said pre-granulate ranges from 20% to 60% by weight.

13. A process for producing the precursor composition according to claim 1, comprising the steps of:
  i. providing an amino acid component comprising at least Valine, Leucine and Isoleucine,
  ii. providing sodium chloride component in dry salt form,
  iii. compounding said amino acid component and sodium chloride component,
  iv. performing granulation of the compound obtained in step iii to form a pre-granulate, comprising a mixture of said amino acid component and said sodium chloride component,
  v. providing as further components glucose and an acid,
  vi. mixing or further compounding and performing a further granulation of components of step v and said pre-granulate obtained in step iv to obtain said precursor composition in dry form
  or
    dissolving said components of step v and said pre-granulate obtained in step iv in water to obtain said precursor composition in liquid form.

14. The process according to claim 13, characterized in that the sodium chloride concentration in said pre-granulate is adjusted to yield a ratio of from 10% to 80% by weight of the total weight of the obtained pre-granulate.

15. A dialysis fluid comprising the amino acids Valine, Isoleucine and Leucine in an amount of

| Amio Acid | Concentration Range |
|---|---|
| Leucine | 300 to 370 µmole/l |
| Isoleucine | 180 to 240 µmole/l |
| Valine | 580 to 680 µmole/l | for use in the treatment of dialysis patients suffering from impaired muscle metabolism and wherein the dialysis fluid is free from Methionine or Tryptophan or both.

16. A method for the treatment of a dialysis patient suffering from impaired muscle metabolism, said method comprising treating said dialysis patient in a dialysis treatment session with a dialysis fluid comprising the amino acids Valine, Isoleucine and Leucine in an amount of

| Amino Acid | Concentration Range |
|---|---|
| Leucine | 300 to 370 μmole/l |
| Isoleucine | 180 to 240 μmole/l |
| Valine | 580 to 680 μmole/l. | wherein the dialysis fluid is free from Methionine or Tryptophan or the dialysis fluid component is free from Methionine and Tryptophan.

\* \* \* \* \*